United States Patent
Serrano Fernandez et al.

(10) Patent No.: US 7,423,171 B2
(45) Date of Patent: Sep. 9, 2008

(54) ONE-STEP CATALYTIC PROCESS FOR THE SYNTHESIS OF ISOCYANATES

(75) Inventors: Francisco Luis Serrano Fernandez, Madrid (ES); Beatriz Almena Munoz, Madrid (ES); Ana Padilla Polo, Madrid (ES); Arancha Orejon Alvarez, Tarragona (ES); Carmen Claver Cabrero, Tarragona (ES); Sergio Castillon Miranda, Tarragona (ES); Pilar Salagre Carnero, Tarragona (ES); Ali Aghmiz, Tarragona (ES)

(73) Assignee: Repsol YPF, S.A., Madrid (ES)

( * ) Notice: Subject to any disclaimer, the term of this patent is extended or adjusted under 35 U.S.C. 154(b) by 0 days.

(21) Appl. No.: 11/765,449

(22) Filed: Jun. 20, 2007

(65) Prior Publication Data

US 2007/0293696 A1 Dec. 20, 2007

(30) Foreign Application Priority Data

Jun. 20, 2006 (EP) .................................. 06380178

(51) Int. Cl.
*C07C 263/00* (2006.01)
(52) U.S. Cl. .................................................... 560/341
(58) Field of Classification Search ........................ None
See application file for complete search history.

(56) References Cited

U.S. PATENT DOCUMENTS

| | | | | |
|---|---|---|---|---|
| 5,194,660 A * | 3/1993 | Leung et al. .................. | 560/24 |
| 2002/0183541 A1 | 12/2002 | Chuang et al. | |
| 2003/0162995 A1 | 8/2003 | Cesti et al. | |
| 2005/0131252 A1 | 6/2005 | Chaudhari et al. | |

FOREIGN PATENT DOCUMENTS

| | | |
|---|---|---|
| JP | 2004262835 A | 9/2004 |
| WO | 9856758 A1 | 12/1998 |
| WO | 9947493 A1 | 9/1999 |

OTHER PUBLICATIONS

Bolzacchini et al., Journal of Molecular Catalysis A: Chemical 111 (1996) 281-287.*
Alper, Howard, et al., "An exceptionally mild, catalytic homogeneous method for the conversion of amines into carbamate esters", "J. Chem. Soc., Chem. Commun.", 1985, pp. 1141-1142.
Bassoli, Angela, et al., "Acyclic and cyclic urea formation via the cobalt-catalysed oxidative carbonylation of aromatic primary amines", "Journal of Molecular Catalysis", 1990, pp. 41-48, vol. 60.
Bolzacchini, Ezio, et al., "Substituent effects in the cobalt-catalyzed oxidative carbonylation of aromatic amines", "Journal of Molecular Catalysis", 1996, pp. 281-287, vol. 111.
Chen, Bei, et al., "CuCl2 and PdCl2 catalysts for oxidative carbonylation of aniline with methanol", "Journal of Molecular Catalysis", 2003, pp. 37-45, vol. 195.

Chisem, Ian C., et al., "Catalytic oxidative of alkyl aromatics using a novel silica supported Schiff base complex", "Chem. Commun.", 1998, pp. 1949-1950.
Choudary, B. M., et al., "Syntheses of interlamellar montmorillonitebipyridinepalladium(II) catalysts: the first examples of chelation in . . . ", "J. Chem. Soc., Chem. Commun.", 1987, pp. 1505-1506.
Corriu, Robert J. P., et al., "Ordered mesoporous hybrid materials containing cobalt(II) Schiff base complex", 2002, pp. 1355-1362, vol. 12.
Dias, A. M. A., et al., "Solubility of oxygen in liquid perfluorocarbons", "Fluid Phase Equilibria", 2004, pp. 325-330, vol. 222-223.
Gupte, Sunil P., et al., "Oxidative carbonylation of aniline over Pd/C catalyst: effect of promoters, solvents and reaction conditions", "Journal of Catalysis", 1988, pp. 246-258, vol. 114.
Kelkar, Ashutosh, et al., "Selectivity behavior in catalytic oxidative carbonylation of alkylamines", "Ind. Eng. Chem. Res.", 1992, pp. 172-176, vol. 31.
Khan, M. M. Taqui, et al., "Oxidative carbonylation of cyclohexylamine to cyclohexylurethane catalysed by dichlorobis-(salicylaldehyde)-o- . . . ", "Journal of Molecular Catalysis", 1990, pp. 303-309, vol. 59.
Kim, Hoon Sik, et al., "Oxidative carbonylation of aromatic amines by selenium compounds", "Journal of Catalysis", 1999, pp. 526-534, vol. 184.
Leung, Tak W., et al., "Oxidative carbonylation of amines catlysed by metallomacrocyclic compounds", "J. Chem. Soc. Chem. Commun.", 1992, pp. 205-206, No. 3.
Li, Kuo-Tseng, et al., "Oxidative carbonylation of aniline using manganese-based catalysts", "Journal of Catalysis", 1993, pp. 631-634, vol. 143.
Maddinelli, Giuseppe, et al., "The bis-(salicylaldehyde)ethylenediimine cobalt(II)-cataylsed oxidative carbonylation of 1-adamantylamine in alcohol . . . ", "Journal of Molecular Catalysis", 1987, pp. 71-77, vol. 39.
Miyazawa, Masahiro, et al., "Palldium-complex-catalyzed decarboxylation-carbonylation of allyl diethylcarbamates", "Synlett", Apr. 1992, pp. 323-324, No. 4.

(Continued)

Primary Examiner—Karl J Puttlitz
(74) Attorney, Agent, or Firm—Steven J. Hultquist; Intellectual Property / Technology Law

(57) ABSTRACT

A one-pot process for the synthesis of isocyanates, polyisocyanates or mixtures thereof which includes the steps of:
  i. preparing a mixture comprising an amine, an alcohol, an oxygen-containing gas, carbon monoxide, a metal complex catalyst selected from the group consisting of macrocyclic complex catalysts and cobalt Shiff base catalysts; and a solvent selected from the group consisting of aliphatic or aromatic halocarbons, perhalogenated alcohols, halogenated ethers, halogenated ketones, perfluorinated hydrocarbons, polymers of chlorotrifluoroethylene having the formula —$(CF_2—CFCl)_n$ wherein n is between 2 and 10, and mixtures thereof;
  ii. subjecting the resulting mixture to a first heating under pressure;
  iii. cooling and depressurizing the mixture resulting from the previous step; and
  iv. subjecting the mixture of the previous step to a second heating to separate out the isocyanate product from the mixture.

23 Claims, No Drawings

OTHER PUBLICATIONS

Orejon, Aranzazu, et al., "Oxidative carbonylation of aniline with new cobalt catalytic systems", "Can. J. Chem.", 2005, pp. 764-768, vol. 83.

Peng, Xingao, et al., "A highly efficient sulfur-catalyzed oxidative carbonylation of primary amines and beta-amino alcohols", "Synlett", 2006, pp. 1161-1164, No. 8.

Prasad, K. Venkatesh, et al., "Activity and selectivity of supported Rh catalysts for oxidative carbonylation of aniline", "Journal of Catalysis", 1994, pp. 204-215, vol. 145.

Riess, Jean G., et al., "Solubility and transport phenomena in perfluorochemicals relevant to blood substitution and other biomedical application", "Pure and Appl. Chem.", 1982, pp. 2383-2406, vol. 54, No. 12.

Selva, Maurizio, et al., "The synthesis of alkyl carbamates from primary aliphatic amines and dialkyl carbonates in supercritical carbon dioxide", "Tetrahedron Letters", 2002, pp. 1217-1219, vol. 43.

Shi, Feng, et al., "A Novel PdCl2/ZrO2/SO2-4 Catalyst for Synthesis of Carbamates by Oxidative Carbonylation of Amines", 2001.

Shi, Feng, et al., "Polymer-immobilized gold catalysts for the efficient and clean syntheses of carbamates and symmetric ureas by . . . ", "Journal of Catalysis", 2002, pp. 548-551, vol. 211.

Shi, Feng, et al., "Silica-gel-confined ionic liquids: a new attempt for the development of supported nanoliquid catalysis", "Chem. Eur. J.", 2005, pp. 5279-5288, vol. 11, No. 18.

Shi, Feng, et al., "The first syntheses of diformamides by carbonylation of aliphatic diamines with Au(I) complex catalysts", "Chem. Commun.", 2001, pp. 345-346.

Sutra, Pierre, et al., "Preparation of MCM-41 type silica-bound manganese(III) Schiff-base complexes", "Chem. Commun.", 1996, pp. 2485-2486.

Toochinda, Pisanu, et al., "Carbamate and dicarbamate synthese from CO/O2/methanol/amines", "Chemical Ind.", 2003, pp. 369-378, vol. 89.

Wan, Boshun, et al., "Polymer-supported palladium-manganese bimetallic catalyst for the oxidative carbonylation of amines to carbamate esters", "Applied Catalysis A: General", 1999, pp. 81-84, vol. 183.

Zhou, Xiang-Ge, et al., "Asymmetric epoxidation of alkenes catalysed by chromium binaphthyl Schiff base complex supported on MCM-41", "Chem. Commun.", 1999, pp. 1789-1790.

* cited by examiner

ONE-STEP CATALYTIC PROCESS FOR THE SYNTHESIS OF ISOCYANATES

CROSS-REFERENCE TO RELATED APPLICATION

The priority of European Patent Application No. EP 06380178.1 filed Jun. 20, 2006 is hereby claimed under the provisions of 35 USC 119. The disclosure of said European Patent Application No. EP 06380178.1 is hereby incorporated herein by reference in its entirety, for all purposes.

FIELD OF THE INVENTION

The present invention is related to the direct conversion of amines into isocyanates, and to a catalytic chemical process for effecting such conversion to produce isocyanates.

BACKGROUND OF THE INVENTION

Isocyanates are important chemicals. For example, the world production of isocyanates exceeded 5 megatons in 2001. Traditionally, isocyanates are manufactured on a commercial scale by reaction of phosgene with amines or amine salts. The reaction, however, has several serious drawbacks. Phosgene is an extremely toxic reagent and a stoichiometric amount of HCl is produced as a by-product. Furthermore, HCl causes serious corrosion, and a stoichiometric amount of NaOH is required to neutralize the HCl, where the same amount of NaCl is formed. As restrictions upon the use of very toxic materials such as phosgene within the chemical industry have become more rigorously enforced, there has been increasing interest in developing alternative methods to phosgene in the synthesis of isocyanate.

As an alternative, the use of dimethyl carbonate or dimethyl sulfate as phosgene substitutes are relatively expensive for commercial applications (see M. Selva et. al., *Tetrahedron Letters*. 2002, 43 (7), 1217-1219; JP 20044262835; WO 98/56758; WO 99/47493).

Many others strategies for non-phosgene routes, including reductive carbonylation and oxidative carbonylation by using CO as carbonyl source, have been reported. One promising alternative approach that has been the subject of research in recent years involves the oxidative carbonylation of amines to carbamates in the presence of an alcohol, usually methanol, followed by catalytic decomposition of the carbamates to isocyanates.

Alper and Hartstock (*J. Chem. Soc., Chem. Commun.* 1141, 1985) disclose catalytic systems including palladium chloride, copper chloride and hydrochloric acid to produce carbamates from amines. This Wacker-type catalytic system, consisting of $PdCl_2$—$CuCl_2$—HCl, is disclosed as being effective at mild conditions (1 atm and room temperature) in the oxidative carbonylation of amines to produce high yields of carbamate. In this system carbon monoxide (CO) and oxygen ($O_2$) are bubbled through an alcohol to which is added $PdCl_2$ and, finally, the amine. The mixture is stirred overnight, at room temperature and pressure, and filtered. The filtrate is subject to rotary evaporation. The resulting oil is treated with either diethyl ether or acetone and filtered, and concentration of the filtrate yields the carbamate ester. Further purification is carried out by thin-layer or column chromatography (silica gel).

Gupte and Chaudhari, *Journal of Catalysis*, 114, 246-258, 1988, studied the oxidative carbonylation of amines using a Pd/C—NaI catalytic system. Although effective at producing carbamates, this catalytic system uses a $CO/O_2$ molar ratio of 5/1, which is inside the flammability envelope.

US 2002/0183541 employ a Group VIII metal catalyst and/or copper-based catalyst with halide promoters to produce carbamate esters through heterogeneous oxidative carbonylation in a gas-solid carbonylation process. The carbamate produced remains on the catalyst surface and must be recovered through expensive extraction and distillation steps.

T. W. Leung, *J. Chem. Soc. Chem. Comm.*, 3, 1992, 205-6 and U.S. Pat. No. 5,194,660 describes a process for producing carbamates, using a homogeneous catalyst that comprises contacting a first reactant selected from primary amine components, secondary amine components, urea components and mixtures thereof; carbon monoxide; at least one oxygen-containing oxidizing agent, in the presence of catalyst composition comprising at least one metal macro-cyclic complex, preferably in the further presence of one iodine component. The macro-cyclic complex is selected from the group consisting of metal porphyrin or metal phthalocyanine including a metal selected from the metals of group IIIa to Va and group VIII of the Periodic Table and at least one iodine component is present in an amount effective to facilitate the formation of the carbamate.

A. Bassoli et al., *J. Mol. Catal.* 1990, 60, 41 teaches the formation of ureas in good yields, with small amounts of carbamates and azo derivatives via the N,N-bis(salicylidene)ethylenediaminocobalt(II)-catalyzed oxidative carbonylation of aromatic primary amines in methanol.

E. Bolzacchini et al., *J. Mol. Catal. A: Chemical*, 111, 1996, 281-287, describes the N,N-bis(salicylidene)ethylenediaminocobalt(II)-catalyzed oxidative carbonylation of substituted aromatic primary amines in methanol to give blends of ureas, isocyanates, carbamates and azoderivatives. Such blends are unsuitable for the synthesis of commercial isocyanates. Further, the long reaction times required (48 hours) precludes the practical industrial application of this approach.

US Patent Application Publication 2003/0162995 describes a one-pot synthesis of isocyanates by reaction of amines with dimethyl carbonate and subsequent heating to obtain the isocyanate. Due to reaction conditions, the separation of the isocyanate product involves a complicated separation process which comprises water addition, further heating, filtration and a number of distillations in order to obtain the isocyanate, in impure form, which then must be further purified.

Therefore, there is an extensive literature regarding the production of isocyanates and polyisocyanates. The most commonly used procedure involves the transformation of an amine into the corresponding carbamate in a first step, followed by the thermal decomposition of the carbamate to obtain the desired isocyanate or polyisocyanate. A large number of prior publications refer to one of these two steps.

For example, as mentioned above, U.S. Pat. No. 5,194,660 discloses a method for the preparation of carbamates. However, the synthesis of the corresponding isocyanates is only suggested and only from the corresponding carbamates after isolation. Further, according to U.S. Pat. No. 5,194,660 it is necessary to isolate the carbamate intermediate prior to its conversion into the desired isocyanate.

Only a few references mention or suggest the possibility of direct transformation of amines into the corresponding isocyanates. However, as in US Patent Application Publication 2003/0162995, they usually require complicated separation steps.

In view of all of the above, there is an existing need to provide an alternative cost-effective and efficient method for the direct synthesis of isocyanates and polyisocyanates.

SUMMARY OF THE INVENTION

An efficient, safe and cost effective one-pot process for the synthesis of isocyanate products has now been surprisingly found.

The one-pot catalytic process disclosed herein satisfies the need in the art for an industrially viable oxidative carbonylation process capable of producing isocyanate products, which at the same time does not require the isolation of intermediate carbamates.

Further, the process according to the present invention does not involve complicated separation steps. The isocyanate products are separated by means of distillation of the reaction mixture and, usually, the isocyanate product is obtained in essentially pure form.

Further, the present invention overcomes to a large extent the hazards associated with the direct reaction of carbon monoxide and oxygen in the presence of organic compounds by dissolving the reactant gases in a reaction solvent (e.g. halocarbons and/or oxygenated fluorinated hydrocarbons).

Therefore, an aspect of the present invention is a one-pot process for the synthesis of isocyanates, polyisocyanates or mixtures thereof, which comprises the steps of:
  i preparing a mixture comprising an amine, an alcohol, an oxygen-containing gas, carbon monoxide, a metal complex catalyst selected from the group consisting of macrocyclic complex catalysts and cobalt Shiff base catalysts and a solvent, selected from the group consisting of aliphatic or aromatic halocarbons, perhalogenated alcohols, halogenated ethers, halogenated ketones, perfluorinated hydrocarbons, polymers of chlorotrifluoroethylene having the formula —$(CF_2-CFCl)_n$ wherein n is between 2 and 10, and mixtures thereof;
  ii subjecting the resulting mixture to a first heating under pressure;
  iii cooling and depressurizing the mixture resulting from the previous step; and
  iv subjecting the mixture of the previous step to a second heating to separate out the isocyanate product from the mixture.

Additional features, aspects and embodiments of the invention will be more fully apparent from the ensuing disclosure and appended claims.

DETAILED DESCRIPTION OF THE INVENTION

It is known that explosive concentration of carbon monoxide in oxygen at 200° C. and atmospheric pressure is between 14.2-95.3%, thus, the range is extremely broad. It is also known that dilution of the gaseous mixture with an inert gas like nitrogen scarcely changes the lower limit concentration. Further, variation of pressure between 1-200 atmospheres and temperatures between 0-200° C. have a modest effect on the explosive range. Furthermore, even when these reactants are brought together in a ratio that, in homogeneous conditions, would be outside the flammability envelope, the establishment of homogeneity from pure components involves at least a temporary passage through the flammability envelope. For these reasons, the explosion risks associated with the direct contact of carbon monoxide and oxygen are not easily mitigated. Furthermore, unfortunately, carbon monoxide and oxygen are only slightly soluble in the alcohols used as solvents and reactants in the prior art, which limits the concentration of these two components in the reaction mixture and thus results in a lower speed of reaction.

In the present invention the solvent is selected from the group of aliphatic or aromatic halocarbons, perhalogenated alcohols, halogenated ethers, halogenated ketones, perfluorinated hydrocarbons, polymers of chlorotrifluoroethylene having the formula —$(CF_2-CFCl)_n$ wherein n is between 2 and 10, and mixtures thereof. These solvents possess high oxygen solubility and allow for a higher concentration of oxygen in reaction mixture at a given oxygen partial pressure. Therefore, by using the solvents of the invention, it is possible to reduce the partial pressure of oxygen and still maintain an acceptable concentration of oxygen in the reaction mixture so that a good speed of reaction can be obtained and, at the same time, the safety of the process is improved by working well outside the flammability envelope and in conditions of lower temperatures and pressures than those used in the prior art.

Halocarbons are preferably aryl halocarbons such as chlorobenzene, dichlorobenzene and trichlorobenzene, fluorocarbons, chlorofluorocarbons, and hydrochlorofluorocarbons. Preferred reaction solvents are the completely fluorine-substituted $C_5$-$C_{10}$ hydrocarbons such as perfluoro-n-hexane, perfluoro-n-heptane, perfluoro-n-nonane, perfluorodecaline or nonafluoro tertbutanol. These liquids are available under various trade names, such as 3M™ Performance Fluids (Minneapolis, Minn.). Polymers of chlorotrifluoroethylene are also commercially available, such as the grade 0.8 of Halocarbon Product Corporation of USA. Those halocarbons can be added to the reaction mixture or at the outlet of the reactor to facilitate the work up of the mixture or to facilitate its cooling.

The halocarbons and particularly fluorinated hydrocarbons are especially inert versus strong oxidizing agents, including oxygen, and dissolve gases readily. For example, it is known that solubility of oxygen in perfluoroalkanes is extremely high (Clark L. C. et al. *Pure Appl. Chem.*, 1982, 54, 2383-2406 and Marrucho, I. M., *Fluid Phase Equilibria*, 222-223, 2004, 325-330). This is the reason why the present process can use lower pressures to achieve the same concentrations of the reactive gases in the liquid medium of reaction compared with the prior art processes that produce carbamates, and easily avoids gaseous environment containing any explosive mixture of reactants above the liquid reaction system.

According to a preferred embodiment, solvents are oxygenated fluorinated hydrocarbons (e.g. fluorinated alcohols and its blends with fluorinated ethers and/or ketones), where at least one alkyl hydrogen of the homologous oxygenate is substituted for fluorine. Preferred oxygenated fluorinated hydrocarbons include, without limitation, 2,2,2-trifluoroethanol, 2,2,3,3 -tetrafluoro-1-propanol, 1,1,1,3,3,3-hexafluoropropan-2-ol, fluorophenols and mixtures thereof, preferably 2,2,2-trifluoroethanol. One preferred fluorinated ether is nonafluorobutyl methyl ether. One preferred fluorinated ketone is hexafluoroacetone.

According to a most preferred embodiment, the preferred solvents can be defined on the basis of their oxygen solubility measured in molar fraction of oxygen in the solvent. Thus, preferred solvents are those falling within the oxygen solubility range of $10^{-5}$ to $10^{-1}$ (limits of the range included in this and in the next cases); more preferred solvents are those falling within the range $5 \cdot 10^{-5}$ to $5 \cdot 10^{-1}$; even more preferred solvents are those falling within the range $10^{-4}$ to $5 \cdot 10^{-2}$; finally, the most preferred solvents are those falling within the range $4 \cdot 10^{-4}$ to $7 \cdot 10^{-3}$ as, for example, perfluoro-n-hexane, perfluoro-n-heptane, perfluoro-n-nonane, perfluorodecaline, 1,1,1,3,3,3-hexafluoropropan-2-ol and 2,2,2-tri-fluoroetanol.

In order to carry out the oxidative carbonylation, the presence of an alcohol is necessary since it acts as a reagent in the process of the invention. According to one preferred embodiment, such alcohol is a perhalogenated alcohol. As mentioned above, perhalogenated alcohols are good oxygen solvents. Therefore, perhalogenated alcohols can be present in the mixture of step i. in more than stoichiometric amount, and at the same time act as both, as reactant and as (co)solvent.

The feed and oxidizing agent can be dissolved in the reaction solvent in any order or fed simultaneously in separate streams to the reaction solvent. For example, it is possible to dissolve oxygen in the reaction solvent to saturation and subsequently contact the resulting oxygen-saturated reaction solvent with the aromatic amine, the catalyst and carbon monoxide in a tubular mixer. Using the reaction solvents described above, the carbon monoxide solubility is generally affected to only a minor extent by the presence of oxygen in the reaction solvent.

In a further embodiment, risk of gas-phase contacting of reactants may also be eliminated by independently dissolving oxygen in the reaction solvent and carbon monoxide in the aromatic amine or polyamine. In this case, the dissolution steps may be carried out, for example, in separated stirred tanks before mixing all the reagents. Thus, it is not necessary to dissolve all the reagents in the same reaction vessel or at the same time. It is certainly possible that the reaction solvent containing previously dissolved reactants can be passed through a fixed bed of catalyst or reacted in a slurry reactor. In the latter case, mechanical agitation (e.g. stirring, shaking, vibrating, etc.) can be used to effect the contacting between the catalyst and the reactants. It is also possible to use a liquid fluidized bed of catalyst, using a flow of gaseous carbon monoxide as described in *"Perry's Chemical Engineers' Handbook*, Sixth edition", 1984 pages 4-25, 4-26, 20-3 and 20-58 to 20-75.

According to one embodiment, the temperature during the first heating is in a range of from 100 to 200° C., preferably from 120 to 180° C., and pressure is in a range of from 5 to 100 bar, preferably from 20 to 70 bar. These conditions assure an effective oxidative carbonylation. The reaction time can vary depending on the reaction system employed, catalyst and other reaction conditions chosen. A typical reaction time is in the range of from about one minute to about 3 hours.

According to a further embodiment, after the reaction mixture is cooled, the temperature during the second heating is in a range of from 50 to 240° in order to separate the solvent by distillation and recover the isocyanate product. Between step iii and iv an additional step comprising separating the catalyst from the reaction mixture may be optionally performed.

According to a further embodiment, the separation of the solvent (step iv.) can be done through one, two or more, preferably two, consecutive distillation processes. Depending on the relative boiling points and nature of the isocyanate product and the solvents used, it is possible to directly obtain the isocyanate product by heating and subsequent distillation(s). Once the isocyanate product has been separated, without further treatment, the solvent may be recovered by a second subsequent distillation(s) of the mixture resulting from the first distillation(s). If the boiling point of the solvent is lower than the boiling point of the isocyanate product, it is possible to carry out a first distillation(s) to recover the solvent, followed by separation of the isocyanate product. Other combinations will be apparent to the skilled person depending on the relative boiling points and nature of the isocyanate product and the solvents used. In any case, the solvent recovered may be recirculated for use in further reactions.

According to a further embodiment, the first distillation(s) is carried out at a temperature in a range of from 50 to 180° C. and under a pressure in a range of from 0.1 to 10 bar, and the second distillation(s) is carried out at a temperature in a range of from 140 to 240° C. and under a pressure in a range of from 1 to 900 mbar. The condensation heat of the solvent from the first apparatus can be used for partially vaporizing solvent in the second apparatus. Recovered reaction solvent that is generated by this separation is normally most economically returned to the reaction solvent phase of the reactor for further reactions.

According to a further embodiment, prior to the second heating (step iv.), it is possible to add a cosolvent to the reaction mixture, for example, 1,2-dichlorobenzene or 1,2,4-trichlorobenzene. The addition of the cosolvent further facilitates the dissolution of the carbamate intermediate and the ulterior separation of the isocyanate product with higher purity. In this way, the work-up of the reaction becomes easier.

The raw isocyanates obtained, can be purified, if desired, in a column with a top pressure of from 1 to 950 mbar, preferably from 5 to 250 mbar, and a bottom temperature of 60-250° C., with the pure isocyanates flow being withdrawn in liquid or gaseous form, preferably in a side-stream of the column.

It has been found that the isocyanate products obtained following the process of the present invention are essentially pure and without the need of further purification. Therefore, the process of the present invention provides a simple way for the industrial synthesis of isocyanate products without the need to isolate and/or purify intermediate products to achieve good yields and purity of isocyanates.

The process according to the present invention can be carried out either batch-wise or in a continuous process by removing continuously the reaction mixture from the reaction system while continuously feeding the reactants into the reaction system. According to one embodiment of the invention, the process is a continuous process wherein space velocity is in a range of from 20 to 40.000 $h^{-1}$ and the distilled solvent is recycled into the reaction.

Suitable amines and polyamines to be converted into isocyanates according to the invention include substituted and unsubstituted aryl amines, for example, aniline, toluidine, 3,3'-dimethyl-4-4'-diphenylamine, phenylendiamines, toluendiamines, 2-4'- and 4,4'-methylendianiline, sulfonyldianilines, thiodianilines, diaminodiphenylmethanes and higher homologs polyaminopolyphenylmethanes, m-phenylenediamine, 1,5-naphthylenediamine and the like, and mixtures thereof; and substituted and unsubstituted aryl diamines or higher functionality polyamines like toluendiamines, diaminodiphenylmethanes or polyaminopolyphenylmethanes or any mixture thereof.

The metal of the catalyst according to the present invention preferably is a metal selected from the metals of Group VIII and more preferably the metal is cobalt. According to one embodiment of the present invention, the metal complex catalyst is selected from a cobalt porphyrin of formula I Formula I

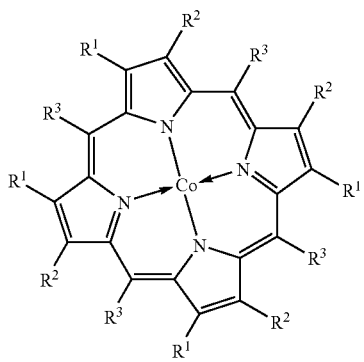

wherein
R¹ and R² are each independently selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl; or R¹ and R² together form a substituted or unsubstituted cycloalkyl, substituted or unsubstituted cycloalkenyl, substituted or unsubstituted cycloalkynyl, substituted or unsubstituted aryl, substituted or unsubstituted heterocyclyl;

R³ is selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl;

or a cobalt phthalocyanine of formula II

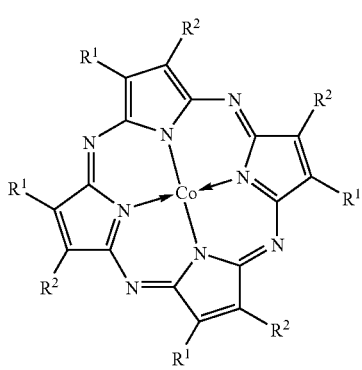

Formula II wherein
R¹ and R² have the same meaning as in formula I;

or a cobalt Shiff base catalyst of formula III

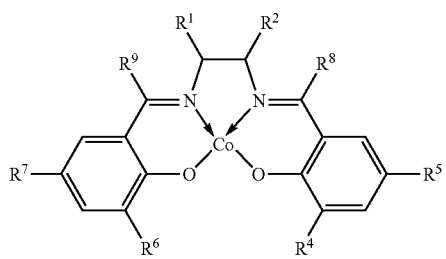

Formula III wherein
R¹ and R² have the same meaning as in formula I;

R⁴, R⁵, R⁶ and R⁷ are each independently selected from hydrogen, cyano, substituted or unsubstituted linear alkyl, substituted or unsubstituted branched alkyl, substituted or unsubstituted alkoxy, —O—Si—R¹⁰, wherein R¹⁰ is a substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl;

R⁹ and R⁸ are each independently selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl;

or mixtures thereof.

According to one preferred embodiment, R⁵ and R⁷ are each a $C_1$-$C_4$-alkoxy group.

According to another preferred embodiment, R⁴, R⁵, R⁶ and R⁷ are each independently selected from a substituted or unsubstituted branched alkyl group.

According to one preferred embodiment, the catalyst of the invention comprises a solid support. Catalyst supports can provide high surface area to disperse active catalyst components and immobilize the active catalyst components and allow an easy recovery of the catalyst. When carbon monoxide, oxygen and the amine react on the catalyst surface, the reaction products migrate into the organic phase, from which isocyanate products can be recovered by conventional distillation. Useful supports are well known in the art and may include, by way of non-limiting example, activated carbon and/or clay, i.e., montmorillonite; polymer supports such as poly(styrene-divinylbenzene), polystyrene, and polyimide; mesoporous materials such as zeolite, MCM-41, ZSM-5, HZSM-5, ammonium ZSM-5 and SBA-15; and metal oxides such as gamma-$Al_2O_3$, $SiO_2$ and $TiO_2$, and MgO, silica or inorganic refractory metal oxides.

Such supported catalysts can be prepared by known methods. For example, Co-clay can be prepared by anchoring the salen ligand in the interlayers of montmorillonite and subsequent complexation with cobalt acetate by the method described by Choudhari et al. (*J. Chem. Soc., Chem. Com-*

*mun.*, 1987, 1505); the immobilization of Co-salen derivatives on mesoporous silica gel and MCM-41 by using grafting reactions, for example, according to I. C. Chisem et al., *Chem. Commun.* 1998, 1949; P. Sutra et al. *Chem. Commun.* 1996, p. 2485; X.-G Zhou et al. *Chem. Commun.* 1999, 1789 or R. J. P. Corriu et al., *J. Mater. Chem.*, 2002, 12, 1355-1362 or by the method described in US Patent Application Publication 2005/0131252.

Further, the process of the present invention can be carried out in the absence or in the presence of a promoter. According to one embodiment, the halide promoter can be selected from alkali metal halides, alkaline earth metal halides, onium halides, compounds capable of forming onium halides at the contacting conditions, oxo acids of halogen atom and their salts, organic halides and halogen molecules. Those compounds containing iodine are particularly preferred. These include KI, NaI, LiI, CsI, tetrabutylammonium iodine, tetraheptyl ammonium iodide, iodous acid, iodine and the like.

In the above definition of the process and compounds and in the description and claims the following terms have the meaning indicated:

"One-pot" refers to processes which do not involve isolation of any intermediates prior to recovery of the final product, regardless of the number of steps required.

The term "under pressure" is understood as a pressure above atmospheric pressure, that is, above 1 atmosphere.

"Essentially pure" refers to compounds which require no purification prior to further use. Typically, a product having purity higher than 98% w/w is considered essentially pure. However, for some applications isocyanate products having purity higher than 95% w/w are also considered essentially pure.

"perhalogenated" refers to organic molecules in which hydrogen is substituted in two or more positions by a halogen group, preferably in all positions. For example, perhalogenated alkyl groups are those in which at least two hydrogen atoms are substituted by a halogen atom, e.g., chlorine, bromine, iodine, or fluorine.

"halogenated" refers to organic molecules in which hydrogen is substituted in at least one position by a halogen group. Therefore, perhalogenated molecules are comprised within the group of halogenated molecules.

"isocyanate product" refers to the products obtained by putting into practice the process according to the present invention, including isocyanates and polyisocyanates.

"Alkyl" refers to a straight or branched hydrocarbon chain radical consisting of carbon and hydrogen atoms, containing no saturation, having 1-12, preferably one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as halo, hydroxy, alkoxy, OPr, OBn, OBz, carboxy, cyano, carbonyl, acyl, alkoxycarbonyl, amino, imino, nitro, mercapto and alkylthio.

"Alkoxy" refers to a radical of the formula —ORa where Ra is an alkyl radical as defined above, e.g., methoxy, ethoxy, propoxy, butoxy etc.

"Aryloxy" refers to a radical of formula —ORb wherein Rb is an aryl radical as defined below.

"Amino" refers to a radical of the formula —NH$_2$, —NHRa, —NRaRb.

"Aryl" refers to an aromatic hydrocarbon radical such as phenyl, naphthyl or anthracyl. The aryl radical may be optionally substituted by one or more substituents such as hydroxy, mercapto, halo, alkyl, phenyl, alkoxy, haloalkyl, nitro, cyano, dialkylamino, aminoalkyl, acyl and alkoxycarbonyl, as defined herein.

"Aralkyl" refers to an aryl group linked to an alkyl group, such as benzyl and phenethyl.

"Alcohol" makes reference to an alkyl comprising 1 to 12 carbon atoms and substituted by at least one hydroxyl group.

"Cycloalkyl" refers to a saturated carbocyclic ring having from 3 to 8 carbon atoms.

"Heterocyclyl" refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidized; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, and tetrahydrofuran.

"Aromatic halocarbon" in the present invention refers to compounds comprising an aromatic residue substituted with on or more halogen atoms.

"Complex" refers to a molecule which is formed by two components: a donor and an acceptor. Bonding between both components to form the complex is possible because the donor may donate an unshared pair of electrons or electrons on $\pi$ orbitals, which the acceptor can accommodate. In a complex more than one donor and/or more than one acceptor are possible. Also, in the same "complex" one donor may be bonded to more than one acceptor and vice versa. Besides the donor-acceptor interactions described above, other types of bonding known to the skilled person, such as covalent bonding, may exist between the donor and the acceptor.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-12 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group can have a substituent at each substitutable position of the group, and each substitution is independent of the other.

Unless otherwise stated, the compounds obtainable by the process of the invention are also meant to include compounds which differ only in the presence of one or more isotopically enriched atoms. For example, compounds obtainable by the process of the invention having the same structures except for the replacement of a hydrogen by a deuterium or tritium, or the replacement of a carbon by a $^{13}C$- or $^{14}C$-enriched carbon or $^{15}N$-enriched nitrogen are within the scope of this invention.

The invention will be further illustrated by means of examples, which should not be interpreted as limiting the scope of the claims.

EXAMPLES

Example 1

General Procedure for the Formation of a Schiff Base-Type Ligand Catalyst

An aldehyde is refluxed in the presence of the corresponding diamine (2:1 molar ratio) in ethanol 95%. Filtration and further washing with absolute ethanol afforded the essentially pure Schiff base-type ligand.

The Schiff base-type ligand obtained above is refluxed in an alcoholic solution together with an aqueous solution of Co(OAc)$_2$. 4H$_2$O under inert atmosphere. Although a crystalline precipitate immediately appeared, refluxing continues for about an hour. The precipitate obtained is filtered under vacuum, washed with water, ethanol and ether, and then dried under vacuum.

Example 2

Immobilization of the Catalyst to a Solid Support

N,N'-(bis(3,5-di-tert-butyl-salicylidene)ethylenediamino) cobalt (II) [Co-tBu-Salen], 1.9 g, prepared following the procedure of Example 1, is added to 125 ml of 2-propanol with stirring, and the mixture heated to 70° C. Powdered silica (5 g, Grace Davison XPO 2407, specific surface area 250 m$^2$/g) is added to the solution and temperature and the stirring are maintained for a further 5 hours. The suspension is filtered, the solid residue is washed with 25 ml dichloromethane anhydrous, twice, and finally dried under vacuum for 5 hours.

Example 3

Comparative Example

A mixture of the aniline (13.2 mmol), the cobalt complex [Co-tBu-Salen] (0.25 mmol) prepared following Example 1, NaI (2,72 mmol) and 1-butanol (20 ml) is charged in a 100 ml autoclave. The autoclave is flushed with carbon monoxide and oxygen in a volumetric ratio of 19/1 to a total pressure of 52.7 bar. The temperature is increased to 110° C. The reaction is maintained under constant vigorous stirring for three hours. After 3 hours the reactor is cooled to room temperature, depressurised and 97.8 g of 1,2-Dichlorobenzene (DCB) is charged in the reactor. The temperature is increased to 180° C. under atmospheric pressure. No 1-butanol is recovered by condensation of the vapours. Analysis of the reaction residue confirms the existence of urea derivatives but no traces of phenylisocyanate can be found.

Example 4

Synthesis of Phenylisocyanate

In a 1000 ml high-pressure stirred autoclave 15.5 g of aniline, 7.6 g of the [Co-tBu-Salen]/Silica catalyst of Example 2, 1.78 g of NaI and 488 g of 2,2,2-trifluoroethanol (TFE) are charged. The autoclave is pressurized with carbon monoxide and oxygen in a volumetric ratio of 19/1. The temperature is increased to 120° C. and the total pressure is maintained constant at 40 bars. The reaction is maintained under constant vigorous stirring for three hours. After 3 hours the reactor is cooled to room temperature, depressurized and 97.8 g of 1,2-dichlorobenzene (DCB) is charged in the reactor. The temperature is increased to 180° C. under atmospheric pressure. The vapors of TFE are separated, condensed, and reused in the following example. In the bottom of the reactor a mixture of DCB and phenylisocyanate is obtained. From this mixture pheylisocyanate is recovered by distillation with 99% w/w purity.

Yield of the intermediate carbamate was 94% and yield of the final isocyanate was 54.6% (51.3% overall yield).

Example 5

Synthesis of 2,4-toluendiisocyanate

In a 1000 ml high-pressure stirred autoclave 10 g of 2,4-toluendiamine (TDA), 7.6 g of [Co-tBu-Salen]/Silica catalyst of Example 2, 1.7 g of NaI and 484 g of 2,2,2-trifluoroethanol (TFE) are charged. The autoclave is pressurized with carbon monoxide and oxygen in a volumetric ratio of 19/1. The temperature is increased to 120° C. and the total pressure is maintained constant at 40 bars. The reaction is maintained under constant vigorous stirring for three hours. After 3 hours the reactor is cooled to room temperature, depressurized and 97.8 g of 1,2-dichlorobenzene (DCB) is charged in the reactor. Then the temperature is increased to 180° C. under atmospheric pressure. The vapors of TFE are separated, condensed, and reused in the following example. In the bottom of the reactor a mixture of DCB and 2,4-toluendiisocyanate is obtained. From this mixture 2,4-toluendiisocyanate is recovered by distillation with 99% w/w purity.

Yield of the intermediate carbamate was 84.1% and yield of the final isocyanate was 83% (69.8% overall yield).

Example 6

Synthesis of 2,4-toluendiisocyanate

In a 350 ml high-pressure stirred autoclave 2 g of 2,4-toluendiamine (TDA), 0.37 g of N,N'-(bis(3,5-di-tert-butyl-salicylidene)ethylenediamino)cobalt (II) [Co-tBu-Salen], synthesized as described in Example 1, 0.18 g of NaI and 48.7 g of 2,2,2-trifluoroethanol (TFE) are charged. The autoclave is pressurized with carbon monoxide and oxygen in a volumetric ratio of 19/1. The temperature is increased to 120° C. and the total pressure is maintained constant at 40 bars. The reaction is maintained under constant vigorous stirring for three hours. After 3 hours the reactor is cooled to room temperature, depressurized and 97.8 g of 1,2-dichlorobenzene (DCB) is charged in the reactor. The temperature is increased to 180° C. under atmospheric pressure. The vapors of TFE are separated, condensed, and reused in the following example. In the bottom of the reactor a mixture of DCB and 2,4-toluendiisocyanate is obtained. From this mixture 2,4-toluendiisocyanate is recovered by distillation with 99% w/w purity.

Yield of the intermediate carbamate was 82% and yield of the final isocyanate was 78% (64% overall yield).

Example 7

Synthesis of 2,4-toluendiisocyanate

In a 350 ml high-pressure stirred autoclave 1 g of 2,4-toluendiamine (TDA), 0.2 g of (±)-Trans-N,N'-bis(3,5-di-tert-butylsalicylidene)-1,2-cyclohexanediamino cobalt (II), synthesized as described in Example 1, 0.18 g of NaI and 48.9 g of 2,2,2-trifluoroethanol (TFE) are charged. The autoclave is pressurized with carbon monoxide and oxygen in a volumetric ratio of 19/1. The temperature is increased up to 120° C. and the total pressure is maintained constant at 40 bars. The reaction is maintained under constant vigorous stirring for three hours. After 3 hours the reactor is cooled to room temperature, depressurized and 97.8 g of 1,2-dichlorobenzene (DCB) is charged in the reactor. The temperature is increased to 180° C. under atmospheric pressure. The vapors of TFE are separated, condensed, and reused in the following example. In the bottom of the reactor a mixture of DCB and 2,4-toluendiisocyanate is obtained. From this mixture 2,4-toluendiisocyanate is recovered by distillation with 99% w/w purity.

Yield of the intermediate carbamate was 88.1% and yield of the final isocyanate was 62.4% (55% overall yield).

What is claimed is:

1. A one-pot process for the synthesis of isocyanates, polyisocyanates or mixtures thereof, which comprises the steps of:
   i. preparing a mixture comprising an amine, an alcohol, an oxygen-containing gas, carbon monoxide, a metal complex catalyst selected from the group consisting of macrocyclic complex catalysts and cobalt Shiff base catalysts; and a solvent selected from the group consisting of aliphatic or aromatic halocarbons, perhalogenated alcohols, halogenated ethers, halogenated ketones, perfluorinated hydrocarbons, polymers of chlorotrifluoroethylene having the formula —$(CF_2-CFCl)_n$, wherein n is between 2 and 10, and mixtures thereof;
   ii. subjecting the resulting mixture to a first heating under pressure;
   iii. cooling and depressurizing the mixture resulting from the previous step; and
   iv. subjecting the mixture of the previous step to a second heating to separate out an isocyanate product from the mixture.

2. The process according to claim 1, wherein said solvent is selected from the group consisting of 2,2,2-trifluoroethanol, 2,2,3,3-tetrafluoro-1-propanol, 1,1,1,3,3,3-hexafluoropropan-2-ol, perfluoro-n-hexane, perfluoro-n-heptane, perfluoro-n-nonane, perfluorodecaline, nonafluoro tertbutanol, and mixtures thereof.

3. The process according to claim 2, wherein the solvent is 2,2,2-trifluoroethanol.

4. The process according to claim 1, wherein the alcohol is present in more than stoichiometric amounts so as to act as both (co)solvent and reactant.

5. The process according to claim 1, wherein the temperature in said first heating is in a range of from 100 to 200° C., and the pressure is in a range of from 5 to 100 bar.

6. The process according to claim 5, wherein the temperature in said first heating is in a range of from 120 to 180° C., and the pressure is in a range of from 20 to 70 bar.

7. The process according to claim 1, wherein the temperature in said second heating is in a range of from 50 to 240° C.

8. The process according to claim 1, wherein a cosolvent is added prior to said second heating.

9. The process according to claim 1, wherein step iv. comprises at least one distillation to remove solvents and at least one distillation to separate the isocyanate product.

10. The process according to claim 9, wherein said distillations are independently selected from distillations under pressure, distillations under vacuum and distillations at atmospheric pressure.

11. The process according to claim 9, wherein said first distillation is carried out at a temperature in a range of from 50 to 180° C. and under a pressure in a range of from 0.1 to 10 bar, and said second distillation is carried out at a temperature in a range of from 140 and 240° C. and under a pressure in a range of from 1 to 900 mbar.

12. The process according to claim 9, characterised in that the distilled solvents are recycled for further reactions.

13. The process according to claim 1, comprising a continuous process.

14. The process according to claim 13, wherein the space velocity is in a range of from 20 to 40.000 $h^{-1}$.

15. The process according to claim 13, wherein the distilled solvent is recycled into the reaction.

16. The process according to claim 1, wherein the metal of the metal complex catalyst is selected from metals of Group VIII.

17. The process of claim 1, wherein the metal complex catalyst is selected from the group consisting of cobalt porphyrins of formula I

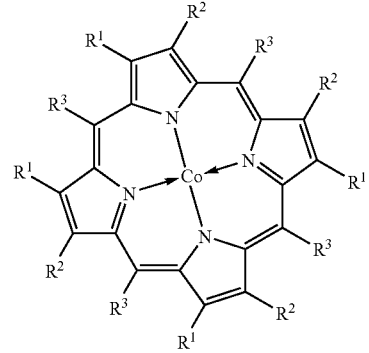

formula I wherein
  $R^1$ and $R^2$ are each independently selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl; or
  $R^1$ and $R^2$ together form a substituted or unsubstituted cycloalkyl, substituted or unsubstituted cycloalkenyl, substituted or unsubstituted cycloalkinyl, substituted or unsubstituted aryl, substituted or unsubstituted heterocyclyl;
  $R^3$ is selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl;

a cobalt phthalocyanine of formula II

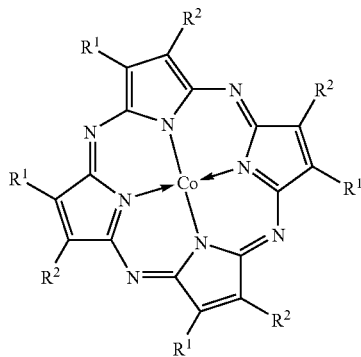

formula II wherein
$R^1$ and $R^2$ have the same meaning as in formula I; and
a cobalt Shiff base catalyst of formula III

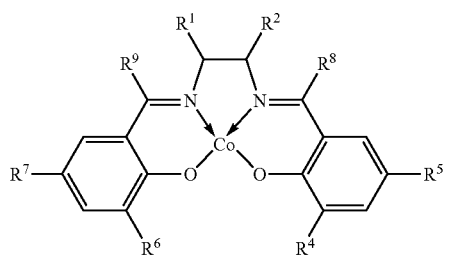

formula III wherein
$R^1$ and $R^2$ have the same meaning as in formula I;
$R^4$, $R^5$, $R^6$ and $R^7$ are each independently selected from among hydrogen, cyano, substituted or unsubstituted linear alkyl, substituted or unsubstituted branched alkyl, substituted or unsubstituted alkoxy, —O—Si—$R^{10}$, wherein $R^{10}$ is a substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl;
$R^9$ and $R^8$ are each independently selected from hydrogen, cyano, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heterocyclyl;
and mixtures thereof.

18. The process according to claim 17, wherein $R^4$, $R^5$, $R^6$ and $R^7$ are each independently selected from a substituted or unsubstituted branched alkyl group.

19. The process according to claim 17, wherein $R^5$ and $R^7$ are each independently selected from a $C_1$-$C_4$-alkoxy group.

20. The process according to claim 1, wherein the catalyst comprises a solid support selected from the group consisting of silica, inorganic refractory metal oxides, zeolites, carbon and polymers or mixtures thereof.

21. The process according to claim 1, wherein the amine is selected from the group consisting of substituted or unsubstituted aryl amines, substituted or unsubstituted aryl diamines, polyaminopolyphenylmethanes and mixtures thereof.

22. The process according to claim 21, wherein the amine is selected from the group consisting of toluenediamines, diaminodiphenylmethanes and mixtures thereof.

23. The process according to claim 1, wherein a halide promoter selected from the group consisting of alkali metal halides, alkaline earth metal halides, onium halides, compounds capable of forming onium halides at contacting conditions, oxo acids of halogen atoms and their salts, organic halides and halogen molecules and mixtures thereof, is added prior to the first heating under pressure.

* * * * *

UNITED STATES PATENT AND TRADEMARK OFFICE
CERTIFICATE OF CORRECTION

PATENT NO. : 7,423,171 B2
APPLICATION NO. : 11/765449
DATED : September 9, 2008
INVENTOR(S) : Serrano Fernandez and Francisco Luis It is certified that error appears in the above-identified patent and that said Letters Patent is hereby corrected as shown below:

Page 1, References Cited, OTHER PUBLICATIONS, second column, ninth entry: "catlysed" should be -- catalysed --.

Page 2, References Cited, OTHER PUBLICATIONS, second column, fourth entry: "synthese" should be -- syntheses --.

Column 5, line 5: "2, 2, 2, -tri-fluoroetanol" should be -- 2, 2, 2, -tri-fluoroethanol --.

Column 5, line 54: "Between step" should be -- Between steps --.

Column 6, line 48: "40.000 $h^{-1}$" should be -- 40,000 $h^{-1}$ --.

Column 9, line 33: "perhalogenated" should be -- Perhalogenated --.

Column 9, line 39: "halogenated" should be -- Halogenated --.

Column 14, line 23 (claim 14): "40.000 $h^{-1}$" should be -- 40,000 $h^{-1}$ --.

Column 14, line 60 (claim 17): "cycloalkinyl" should be -- cycloalkynyl --.

Signed and Sealed this

Thirtieth Day of December, 2008

JON W. DUDAS
*Director of the United States Patent and Trademark Office*